United States Patent
Åsemyr

(10) Patent No.: US 6,646,736 B1
(45) Date of Patent: Nov. 11, 2003

(54) METHOD FOR CALIBRATING EQUIPMENT FOR DETECTING IMPURITIES IN TRANSPARENT MATERIAL

(75) Inventor: Göran Åsemyr, Onsala (SE)

(73) Assignee: Semyre Photonic Systems AB, Stenungsund (SE)

( * ) Notice: Subject to any disclaimer, the term of this patent is extended or adjusted under 35 U.S.C. 154(b) by 0 days.

(21) Appl. No.: 09/958,780
(22) PCT Filed: Apr. 10, 2000
(86) PCT No.: PCT/SE00/00683
§ 371 (c)(1), (2), (4) Date: Oct. 12, 2001
(87) PCT Pub. No.: WO00/62044
PCT Pub. Date: Oct. 19, 2000

(30) Foreign Application Priority Data

Apr. 12, 1999 (SE) ................................. 9901293

(51) Int. Cl.⁷ ................................................. G01J 1/10
(52) U.S. Cl. ................................ 356/243.4; 356/239.1; 73/1.81
(58) Field of Search ......................... 356/243.1–243.8, 356/6, 239.8; 73/1.81; 702/155; 348/129, 130; 382/133–136

(56) References Cited

U.S. PATENT DOCUMENTS

| | | | | |
|---|---|---|---|---|
| 5,416,594 A | * | 5/1995 | Gross et al. | ............. 356/237.5 |
| 5,773,951 A | * | 6/1998 | Markowski et al. | ........ 318/625 |
| 5,875,027 A | | 2/1999 | Ishiguro et al. | |
| 5,966,677 A | * | 10/1999 | Fiekowsky | ................... 702/95 |

FOREIGN PATENT DOCUMENTS

WO    WO 97/35338    9/1997

* cited by examiner

Primary Examiner—Richard A. Rosenberger
Assistant Examiner—Vincent P. Barth
(74) Attorney, Agent, or Firm—Nixon & Vanderhye

(57) ABSTRACT

Equipment for detecting impurities in transparent material comprising a light source to illuminate the material, a camera to detect light transmitted through the material and signal-processing apparatus for processing and analysing signals from the camera representing the light transmission through the material. This type of equipment is calibrated by dark areas being displayed on a film of transparent material (22, 24, 26) and the actual sizes (30) of the areas being determined. The sizes of the dark areas are then determined using the detecting equipment (34) and in this way determined sizes are compared with actual sizes (36) for calibration of the detecting equipment (38).

6 Claims, 3 Drawing Sheets

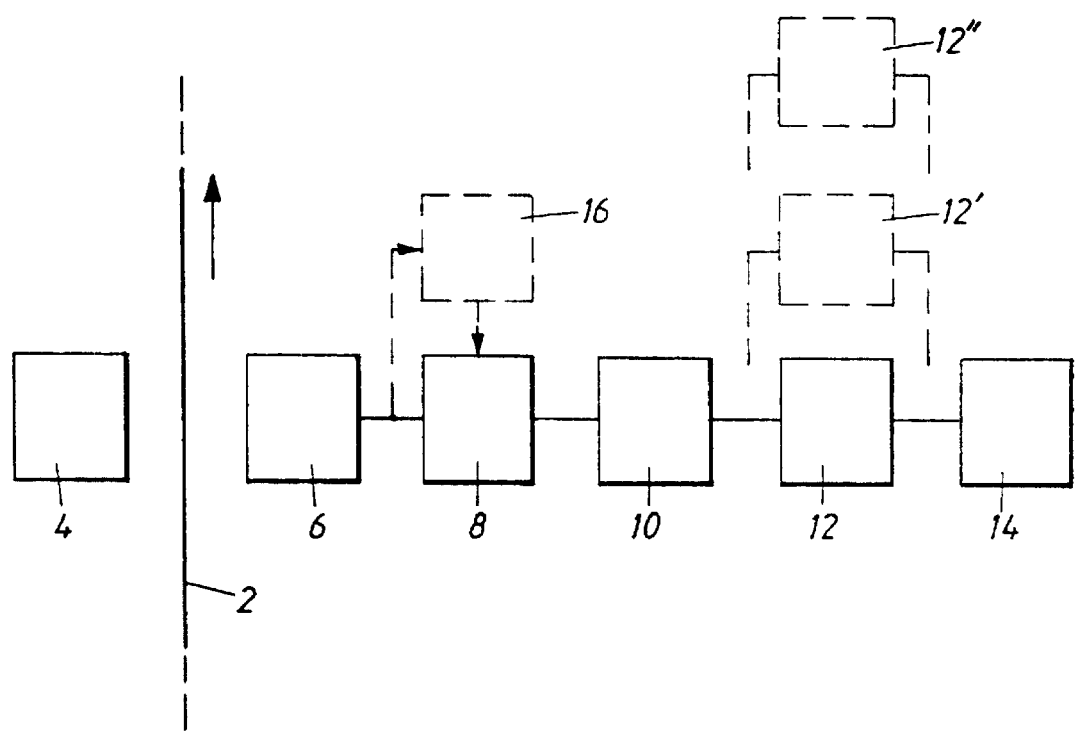

Fig. 3
No 1 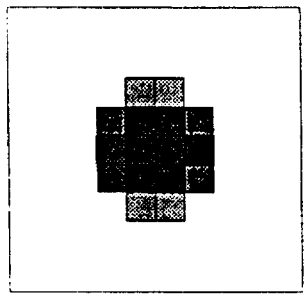
No 6 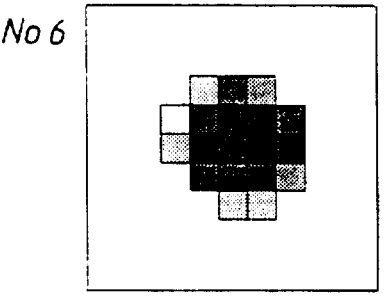
No 2 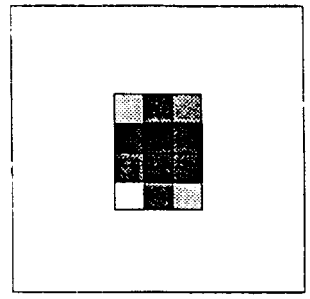
No 7 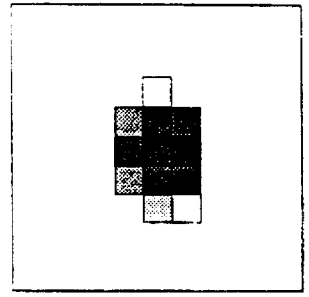
No 3 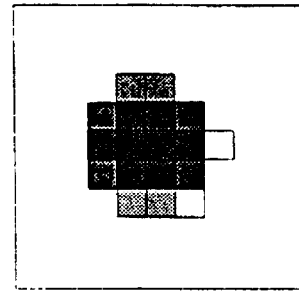
No 8 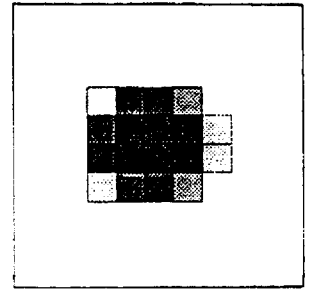
No 4 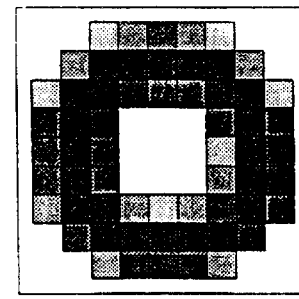
No 9 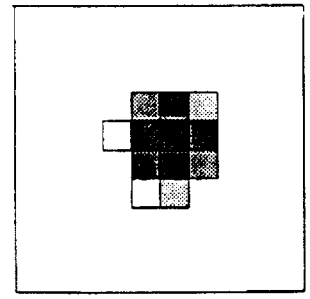
No 5 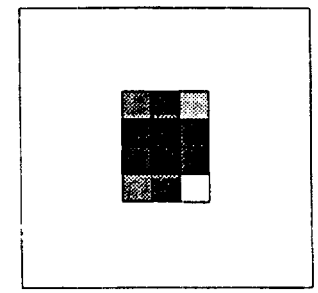
No 10 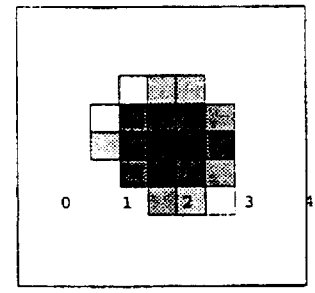

METHOD FOR CALIBRATING EQUIPMENT FOR DETECTING IMPURITIES IN TRANSPARENT MATERIAL

The present invention relates to a method for calibrating equipment for detecting impurities in transparent material, said detecting equipment comprising a light source to illuminate the material, a camera to detect light transmitted through the material and signal-processing apparatus for processing and analysing signals from the camera representing the light transmission through the material.

The above-mentioned equipment for detecting impurities may be, for instance, of the type described in patent application SE 9901291-6 filed simultaneously.

Figure 1:

As can be seen in FIG. 1 such an equipment comprises a light source 4 and a detector 6, between which an extruded polyethylene or polypropylene material 2 is caused to pass. A CCD linear camera is preferably used as detector. The camera 6 emits light transmission data for each individual scanned pixel. An "area of interest" is determined from these data in the material 2, in a first comparator 8 and these "areas of interest" are stored in a buffer memory 10. A reference forming unit 16 is arranged to form a suitable reference value for the comparator 8, in order to determine said "areas of interest" by comparison of the measured values with the reference value.

The buffer memory 10 is read by a digital signal processor 12. Several such processors 12, 12', 12" may possibly be arranged to operate in parallel if necessary. The light transmission data is analysed with the aid of the signal processor 12, to determine the type of impurity as well as its shape and extension. The result of this analysis is then transferred to a system computer 14 to be compiled and reported for classification of the material 2 under inspection, for instance.

The object of the present invention is to provide a method for reliable calibration of this type of detecting equipment, wherein the calibration method can be documented, enabling it to be traced backwards, as is required under the ISO 9000 standard.

This object is achieved with a method of the type described in the introduction having the characteristics defined in claim 1.

The method according to the invention offers a calibration method that is traceable in accordance with the requirements of ISO 9000, and no special adjustment members are needed for the relevant detecting equipment which a user might come into contact with, thereby unintentionally ruining the calibration. The calibration performed by the method according to the invention will thus remain over a period of time.

According to advantageous embodiments of the method according to the invention, said dark areas are produced with predetermined larger sizes on the calibration film, after which the areas are reduced to the desired sizes for the calibration. The spots and rings are reduced, suitably using a repro- or microfilm camera, to sizes in the range of 30–100 $\mu$m. In principle any shape of patches and rings whatsoever can be used and these are made entirely black, i.e. completely untransparent for light, thus allowing the edge to be detected.

According to another embodiment of the method according to the invention, the dark areas are repeated on the calibration film with predetermined spacings so as to enable determination of the standard deviation in the calibration.

According to yet another advantageous embodiment of the method according to the invention, a scale is applied in the measuring position of the detecting equipment, with the aid of which the desired pixel resolution is adjusted and the camera focus fixed on the measuring position before the calibration film is scanned. The scale used for this adjustment is preferably one designed for this purpose, known as Heidenhain scale. After the pixel resolution has been adjusted, the setting of the camera is fixed mechanically with the camera lens focused on the measuring point and the camera adjustment can be maintained like that afterwards.

In order to explain the invention in more detail one embodiment of the method according to the invention will be described more fully by way of example with reference to FIG. 2.

Figure 2:
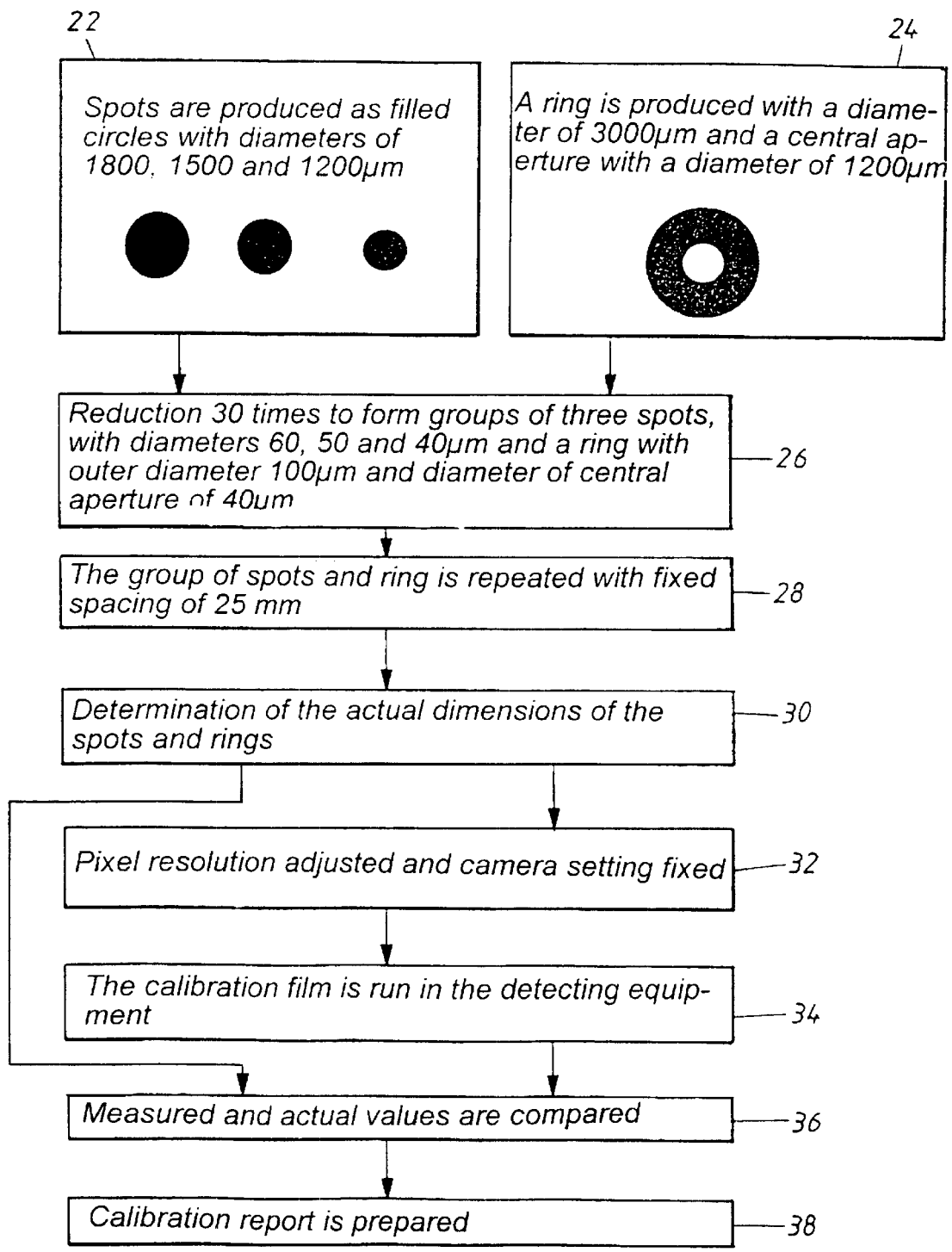

In the drawings FIG. 1 shows a block diagram of an example of a type of detecting equipment in which the method according to the invention can be used, FIG. 2 shows a flow chart illustrating an embodiment by way of example of the method according to the invention and FIG. 3 shows examples of the results of measurements performed using the detecting equipment in question.

With the calibration method according to the invention a calibration film is produced having dark spots, see step 22 in FIG. 2, or rings, see step 24 in Figure 2, of predetermined sizes. These spots and rings are produced on the film on a considerably larger scale than that to be subsequently used. The spots shown at 22 may have diameters of typically 1800, 1500 and 1200 $\mu$m, and the ring in step 24 may have a diameter of typically 300 $\mu$m with a central aperture of 1200 $\mu$m in diameter.

Dark areas or patches shaped differently from the illustrated circular spots and the ring may naturally be used.

The spots and ring are reduced in a repro- or microfilm camera to desired sizes, such as reduction to 30 times smaller to spots sized 60, 50 and 40 $\mu$m and a ring having a diameter of 100 $\mu$m, see step 26.

If completely black spots are used on the calibration film, i.e. spots that allow no light through at all, the edges of the spots can immediately be detected by the camera. If, for instance, a dot having a diameter of 40 $\mu$m passes pixels of 10 $\mu$m in size, the dot can at most cover exactly four pixels. However, at the edge of the dot a grey scale gradually passing to completely black will appear, after which the black with again recede after a few pixels.

A black ring on the calibration tape does not usually cut out the light transmission entirely due to diffraction that gives rise to spread and diffuse light. Neither do available detectors, i.e. cameras, measure down to light transmission zero, that is to say that there is always a certain dark current. A trigger level is therefore chosen that is at a reliable distance above the minimum transmission level. If, for a dark dot with diameter 30 $\mu$m, the average transmission level is 11–12%, the trigger level is suitably chosen to 25% or 35% of the transmission level.

The spots and the ring are then repeated with predetermined spacings. Since the spots, rings, etc. are repeated with predetermined spacings on the calibration film this enables standard deviation also to be determined. On a microfilm, at step 28, for instance, with a fixed spacing of 25 mm, for instance. The calibration film intended for the calibration method is obtained in this way.

The actual dimensions of the spots and rings on the calibration film are thereafter checked using a reading microscope, at step 30.

Before the calibration film is used for the calibration procedure in the detecting equipment, the desired pixel resolution is set with the aid of a glass scale, a Heidenhain scale, as described above. The setting of the camera is then fixed mechanically and need not be adjusted again, at step 32 in FIG. 2. The camera is thus fastened with screws once and for all, aligned with its focus on the scale, i.e. on the measuring position of the equipment, so that the measuring position is in the focus of the camera lens.

The calibration film is then run in the detecting equipment, and the sizes of the spots and rings measured at step 34. FIG. 3 shows examples of results of such measurements performed with the equipment illustrated in FIG. 1 on a film with dark spots of various sizes, and one dark ring.

In step 36, thus, the measured values obtained are compared with sizes of the spots and rings determined in the reading microscope, step 30, in order to calibrate the equipment, and in step 38 a calibration report is finally generated.

What is claimed is:

1. A method for calibrating equipment for detecting impurities in transparent material, said detecting equipment including a light source to illuminate the material, a camera to detect light transmitted through the material and a signal processing apparatus for processing and analyzing signals from the camera representing the light transmission through the material, said method comprising the steps of:

(a) displaying dark areas on a film of transparent material with a predetermined size larger than sizes desired for the calibration;

(b) subsequent to step (a), reducing the dark areas to the desired sizes for the calibration using a repro- or microfilm camera to form a calibration film;

(c) determining the actual sizes of the reduced dark areas;

(d) determining the size of the dark areas on the calibration film using the detecting equipment; and (e) comparing the sizes of the dark areas of step (d) and the actual sizes of the dark areas of step (c) for calibration of the detecting equipment.

2. A method according to claim 1 including using a reading microscope to determine the actual sizes of the reduced areas of step (c).

3. A method according to claim 1 including repeating the dark areas on the calibration film with predetermined spacing to enable determination of the standard deviation in the calibration.

4. A method according to claim 1 including displaying said dark areas in the shape of substantially circular spots or rings.

5. A method according to claim 1 including employing a linear camera in the detecting equipment and emitting signals from said camera representing scanned light transmission data pixel-by-pixel.

6. A method according to claim 5 including, prior to step (d), applying a scale in a measuring position of the detecting equipment, adjusting the desired pixel resolution and fixing the camera focus on the measuring position.

\* \* \* \* \*